US009014806B2

(12) United States Patent
Henry et al.

(10) Patent No.: US 9,014,806 B2
(45) Date of Patent: Apr. 21, 2015

(54) SYSTEM AND METHOD FOR PERFORMING A CAPTURE TEST BASED ON THE ANALYSIS OF A CARDIAC VECTOGRAM

(75) Inventors: Christine Henry, Paris (FR); Paola Milpied, Paris (FR)

(73) Assignee: Sorin CRM SAS, Clamart (FR)

( * ) Notice: Subject to any disclaimer, the term of this patent is extended or adjusted under 35 U.S.C. 154(b) by 317 days.

(21) Appl. No.: 12/949,653

(22) Filed: Nov. 18, 2010

(65) Prior Publication Data

US 2011/0118804 A1    May 19, 2011

(30) Foreign Application Priority Data

Nov. 18, 2009    (FR) ...................................... 09 58137

(51) Int. Cl.
*A61N 1/37*     (2006.01)
*A61N 1/368*    (2006.01)

(52) U.S. Cl.
CPC .............. *A61N 1/371* (2013.01); *A61N 1/3684* (2013.01)

(58) Field of Classification Search
USPC ........................................... 607/9, 17, 27, 28
See application file for complete search history.

(56) References Cited

U.S. PATENT DOCUMENTS

| | | | |
|---|---|---|---|
| 5,179,946 A * | 1/1993 | Weiss | 607/4 |
| 6,438,409 B1 * | 8/2002 | Malik et al. | 600/512 |
| 6,487,451 B1 | 11/2002 | Casset et al. | |
| 6,711,441 B2 | 3/2004 | Limousin | |
| 6,714,820 B2 | 3/2004 | Casset et al. | |
| 6,760,615 B2 * | 7/2004 | Ferek-Petric | 600/518 |

(Continued)

FOREIGN PATENT DOCUMENTS

| | | |
|---|---|---|
| EP | 1080744 | 7/2001 |
| EP | 1216722 | 6/2002 |

(Continued)

OTHER PUBLICATIONS

Foreign Search Report (Annexe Au Rapport De Recherche Preliminaire Relatif a La Demande De Brevet Francais No. FR0958137 FA730043), Apr. 15, 2010.

(Continued)

*Primary Examiner* — Niketa Patel
*Assistant Examiner* — Christopher A Flory
(74) *Attorney, Agent, or Firm* — Foley & Lardner LLP (57) ABSTRACT

Performing a capture test on a stimulated cardiac cycle based on the analysis of a cardiac vectogram using an active medical device including circuits and control logic for delivering electrical stimulation pulses to a heart chamber; collecting electrical activity of the heart chamber and producing two distinct temporal components ($V_{bip}$, $V_{uni}$) from two distinct intracardiac electrogram EGM signals from the heart chamber. The capture test detects an occurrence of a depolarization wave induced by the stimulation of the heart chamber, and determines a two-dimensional non-temporal characteristic (VGM) representative of the stimulated cardiac cycle, from the variation of one of the temporal components ($V_{uni}$) versus the other temporal component ($V_{bip}$). A bi-dimensional analysis delivers at least one descriptor parameter of the two-dimensional non-temporal characteristic, and determines a presence or loss of a capture based on the at least one descriptor parameter.

18 Claims, 6 Drawing Sheets

(56) References Cited

U.S. PATENT DOCUMENTS

| | | | |
|---|---|---|---|
| 7,509,170 B2* | 3/2009 | Zhang et al. | 607/28 |
| 7,979,112 B2* | 7/2011 | Molin et al. | 600/509 |
| 2003/0083587 A1* | 5/2003 | Ferek-Petric | 600/512 |
| 2005/0137638 A1 | 6/2005 | Yonce et al. | |
| 2006/0253164 A1 | 11/2006 | Zhang et al. | |
| 2007/0191895 A1* | 8/2007 | Foreman et al. | 607/14 |
| 2008/0294217 A1 | 11/2008 | Lian et al. | |
| 2009/0076557 A1* | 3/2009 | Zhang et al. | 607/4 |
| 2010/0249626 A1 | 9/2010 | El Arab et al. | |
| 2011/0230776 A1* | 9/2011 | Milpied et al. | 600/516 |

FOREIGN PATENT DOCUMENTS

| | | |
|---|---|---|
| EP | 1287849 | 3/2003 |
| EP | 1995685 | 11/2008 |
| EP | 2105843 | 9/2009 |
| WO | WO9302741 | 2/1993 |

OTHER PUBLICATIONS

Jon Shlens, *A Tutorial on Principal Component Analysis Derivation, Discussion and Singular Value Decomposition*, jonshlens@ucsd.edu, Mar. 25, 2003 Version 1, Mar. 25, 2003, (pp. 1-6 only because too large to upload to USPTO site).

\* cited by examiner

SYSTEM AND METHOD FOR PERFORMING A CAPTURE TEST BASED ON THE ANALYSIS OF A CARDIAC VECTOGRAM

This present application claims the benefit of French Application No. 09-58137 entitled "Active Medical Device Comprising Means of Capture Test by Analysis of the Cardiac Vectrogram" and filed Nov. 18, 2009, which is hereby incorporated by reference in its entirety.

FIELD OF INVENTION

The present invention relates to "active implantable medical devices" as defined by the 20 Jun. 1990 Directive 90/385/EEC of the Council of the European Communities, and more particularly to devices that continuously monitor a patient's heart rhythm and deliver to the heart, if necessary, electrical pulses for stimulation, resynchronization and/or defibrillation in response to a rhythm disorder detected by the devices.

BACKGROUND

Antibradycardia stimulation involves the delivery of controlled stimulation pulses to an atrium and/or a ventricle, using a single or dual chamber device. In the case of cardiac resynchronization therapy ("CRT"), a multisite device delivers the stimulation pulses jointly to both ventricles. In general, after stimulating a cardiac cavity, a test known as a "capture test" is performed to determine whether the stimulation induced a depolarization wave in the cavity (also referred to as an "evoked wave"). A capture test is particularly useful for adjusting the amplitude and/or the width of the stimulation pulses, or the energy delivered to the stimulation site.

There are many techniques for implementing a capture test. For example, a capture test described in WO 93/02741 A1 and its counterpart U.S. Pat. No. 5,411,533 (Sorin CRM, previously known as ELA Medical) uses an automated testing algorithm that measures the efficiency threshold of the stimulation referred to as a "pacing threshold", at regular intervals, for example, every six hours. The amplitude of the stimulation pulse is then adjusted, based on the measured pacing threshold increased by a safety margin taking into account the various uncertainties in determining the pacing threshold.

It has been discovered that this capture test algorithm in known devices can be misled by some atypical situations, such as an occurrence of a fusion event, in which a stimulation is triggered concomitantly by a spontaneous QRS event, at the time the capture test is performed.

Various proposals have been made to overcome this difficulty, including EP 1216722 A1 and its counterpart U.S. Pat. No. 6,711,441 (Sorin CRM, previously known as ELA Medical), which describes detecting a suspected fusion event and disregarding suspected events in the capture test.

Nevertheless, clinical follow-ups of patients show that the different conventional techniques for performing a capture test remain sensitive to various rhythm abnormalities occurring erratically, which deceive the test algorithm and lead to both false positive and false negative results. These anomalies may lead to an incorrect adjustment of the stimulation energy. If the stimulation energy is set too high, more power is consumed than is needed, thus the lifetime of the implant is reduced. If the stimulation energy is set too low, it presents a potential risk to the patient.

It also is known, as disclosed in EP 1287849 A1 and its counterpart U.S. Pat. No. 6,714,820 (Sorin CRM, previously known as ELA Medical), to perform a capture test, and readjust the stimulation energy continuously by checking on each cycle whether the stimulation was effective. These "cycle-to-cycle" adjustment techniques, despite their much higher reactivity, are very sensitive to the occurrence of a fusion event or an isolated atypical cycle, such as a post-atrial ventricular detection, a too short cycle, or an extrasystole, which may be misinterpreted as a loss of a capture, even though the pacing threshold did not naturally increase.

Moreover, in case of a multisite device, it is necessary to run as many capture tests as there are existing test sites. With the recent trend of increasing the number of stimulation sites, this leads to a substantial increase in a test time needed to perform a capture test on all the stimulation sites.

OBJECT AND SUMMARY

The present invention is directed to obtaining relevant parameters for detecting an evoked wave from endocardial electrogram (EGM) signals collected concurrently on two distinct channels from a single cavity, for example, a ventricle. The two distinct EGM channels may be, for example, a unipolar signal (e.g., a signal collected between the device housing and one of the distal or proximal lead electrodes), or a bipolar signal (e.g., a signal collected between a distal electrode and a proximal electrode of the lead).

Characteristically, the analysis of the EGM signals is a two-dimensional analysis of a "cardiac loop" or "vectogram" ("VGM"), which is a representation of one of the two signals relative to the other in a two-dimension space. This two-dimensional space is typically defined by a "unipolar channel" (in ordinate) vs. a "bipolar channel" (in abscissa), and each beat or significant fraction of a beat is represented by its vectogram in the two-dimensional space-eliminating the temporal dimension.

It shall be appreciated by a person of ordinary skill in the art that the "two-dimensional" analysis, or "in two dimensions" (2D) discussed herein is exemplary only, thus should not be seen as restrictive in itself. Rather, the invention may also apply to analysis in a higher order multidimensional space, e.g., 3D or more, by extrapolation of the teachings of the present description to a situation in which EGM signals collected from a cavity are simultaneously collected on three or more channels.

The invention therefore is broadly directed to the detection of an evoked wave by analysis of a recorded VGM during a cardiac cycle, particularly from a measure of the similarity or difference between the recorded VGM during a cardiac cycle under test and that recorded during a reference cardiac cycle corresponding to a well defined and known situation (e.g., proven capture, no capture, fusion). The cardiac cycle under test is also referred to herein as a "stimulated cardiac cycle," as contrasted with the aforementioned "reference cardiac cycle."

More specifically, one aspect of the present invention is directed to an active medical device of a known type including: stimulation means such as circuits that deliver electrical stimulation pulses of low energy to an electrode implanted in a cardiac chamber of a patient; means for detecting (collecting) the patient's heart electrical activity that includes means for producing at least two distinct temporal components from two distinct endocardial electrogram EGM signals of a cavity, and mean for performing a capture test on a stimulated cardiac cycle to detect an occurrence of a depolarization wave induced by the stimulation to the cavity.

Preferably, the means for performing a capture test includes: means for determining a non-temporal 2D characteristic representative of said stimulated cardiac cycle, based upon the variation of one of the temporal components as a function of the other of the temporal components, and means for performing a bi-dimensional analysis for delivering at least one descriptor parameter of said non-temporal 2D characteristic, and for determining a presence or loss of a capture based on said at least one descriptor parameter.

In one embodiment, the means for detecting a patient's electrical heart activity is connected to two or more electrodes of a lead placed in the patient's cardiac chamber(s), and to the device housing, and obtains a bipolar signal and a monopolar signal as said two distinct EGM signals respectively.

In a preferred embodiment, the means for determining the non-temporal 2D characteristic determines the 2D characteristic over time of the components of a fraction of the stimulated cardiac cycle, for example, in a time window including the QRS complex of the stimulated cardiac cycle.

In another embodiment, the means for bi-dimensional analysis compares the 2D characteristic of the stimulated cardiac cycle to at least one reference 2D characteristic, using a descriptor parameter that is representative of a degree of similarity or difference between the stimulated cardiac cycle 2D characteristic and the reference 2D characteristic. In yet another embodiment, the means for bi-dimensional analysis includes means for discriminating a fusion situation based on the at least one descriptor parameter.

According to one embodiment, the descriptor parameter generated by the means for bi-dimensional analysis is a geometric descriptor. For example, the geometric descriptor is:

the angle of a tangent vector to the 2D characteristic considered in a plurality of points of the vectogram. In this case, the means for bi-dimensional analysis includes a means for evaluating a correlation coefficient between the respective angle of the tangent vectors of the stimulated cardiac cycle 2D characteristic and a reference 2D characteristic;

the norm of the tangent vector to the 2D characteristic considered in a plurality of points of the vectogram. In this case, the means for two-dimensional analysis includes means for evaluating a correlation coefficient between the norms of the respective tangent vectors of the stimulated cardiac cycle 2D characteristic and a reference 2D characteristic;

the curvature of the 2D characteristic considered in a plurality of points. In this case, the means for bi-dimensional analysis includes means for evaluating a correlation coefficient between the respective curvatures of the stimulated cardiac cycle 2D characteristic and a reference 2D feature, and/or the area defined by the stimulated cardiac cycle 2D characteristic.

According to one embodiment, several of these parameters are concurrently used when performing an analysis based on a combination of parameters, such as a combination of the norm and the angle of the tangent vector.

In an alternative embodiment, the means for determining a two-dimensional non-temporal characteristic (VGM) includes means for analyzing the principal components and producing the descriptor parameter(s).

The device may be a multisite device, wherein: the stimulation means includes means for selectively delivering pacing to a plurality of stimulation sites, or only to some of the stimulation sites, and the means for detecting includes means for producing, at each site, at least two distinct EGM components, and the means for performing a capture test includes means for discriminating situations among: a presence of capture on all the stimulated sites; a presence of capture only on a subset of the stimulated sites; and a loss of a capture on all the stimulated sites.

BRIEF DESCRIPTION OF THE DRAWINGS

Further features, characteristics and advantages of the present invention will become apparent to a person of ordinary skill in the art from the following detailed description made with reference to the drawings annexed, in which like reference characters refer to like elements and in which.

DETAILED DESCRIPTION

With reference to FIGS. 1-11, an embodiment of a device according to the present invention will now be described.

According to one embodiment, the present invention is implemented in an appropriate programming of a controlling software of a known device, for example, a cardiac pacemaker or a defibrillator/cardioverter, including hardware circuits and a control logic for collecting signals from endocardial leads and/or one or more implanted sensors. The present invention may particularly be implemented in an implantable device such as those of the Reply, Paradym, Ovatio, Esprit or Rhapsody device family manufactured and marketed by Sorin CRM, Clamart France (formerly known as ELA Medical, Montrouge, France).

A suitable implantable device such as those mentioned above includes a programmable microprocessor to receive, format, and process electrical signals collected (detected) by implanted electrodes, and to generate and deliver stimulation pulses to the implanted electrodes. It is possible to transmit by telemetry software and store it in a memory of the implantable device, and execute the software to implement various functions and features of the present invention that are described herein. The adaptation and modification of a device to implement these functions and features of the present invention is believed to be within the abilities of a person of ordinary skill in the art, and therefore will not be described in detail.

As indicated above, the present invention is directed to providing an improved analysis for detecting an evoked wave following a stimulation of a cavity from electrogram signals (EGM) collected on two different channels in a two-dimensional space.

Figure 1:
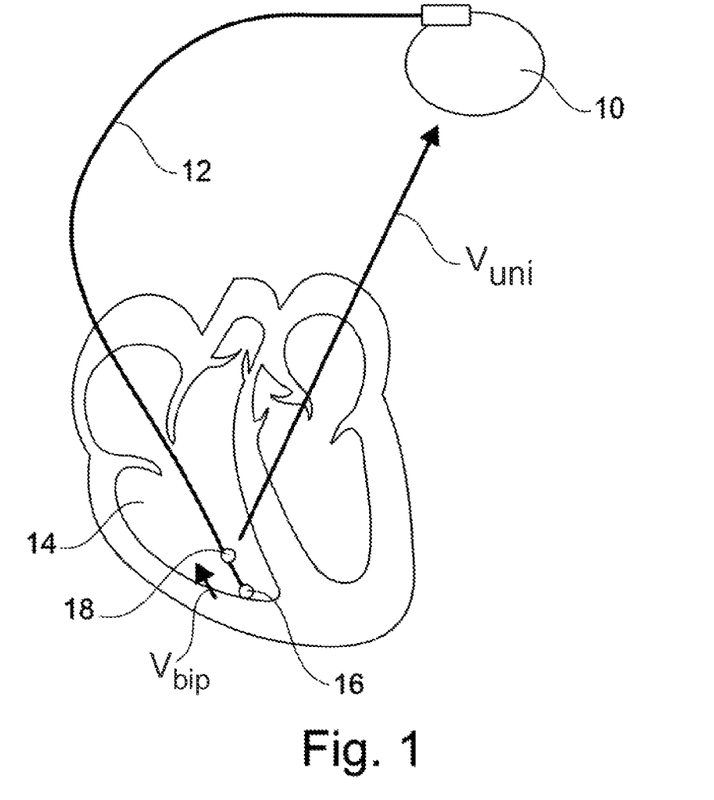
FIG. 1 is a schematic view of a bipolar lead located at an apex of the ventricle.

FIG. 1 illustrates a conventional "single chamber" configuration for providing stimulation pulses to a cardiac cavity. A pulse generator 10 is connected to a lead 12 located in a patient's right ventricle 14. The lead 12 has two electrodes including a distal electrode 16 and a proximal electrode 18 for collecting a first electrogram $V_{bip}$ corresponding to the potential difference between the distal electrode 16 and the proximal electrode 18, and a second electrogram $V_{uni}$, corresponding to the potential difference between one of the electrodes, e.g., the proximal electrode 18 and the metal housing of the pulse generator 10.

This single chamber configuration was shown because of its simplicity to describe the present invention, but is in no way intended to be limiting as to the scope of the present invention. The present invention may be applied to the detection of a capture during stimulation of an atrium by a suitable electrode, or to the concomitant stimulation of both right and left ventricles in the case of multisite devices, especially biventricular devices designed to restore synchronization between the two ventricles. In general, the term "cavity" as used herein should be understood to mean either the atrium or ventricle, in the right or left cardiac cavities.

Figure 2A:
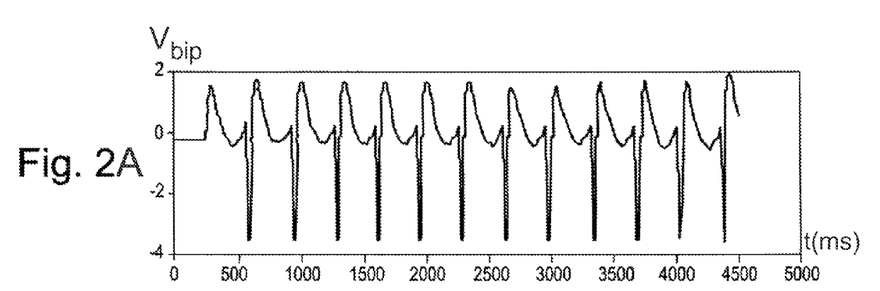
FIG. 2 illustrates exemplary EGM signals obtained respectively from the ventricular bipolar and unipolar channels according to the configuration of FIG. 1.
Figure 2B:
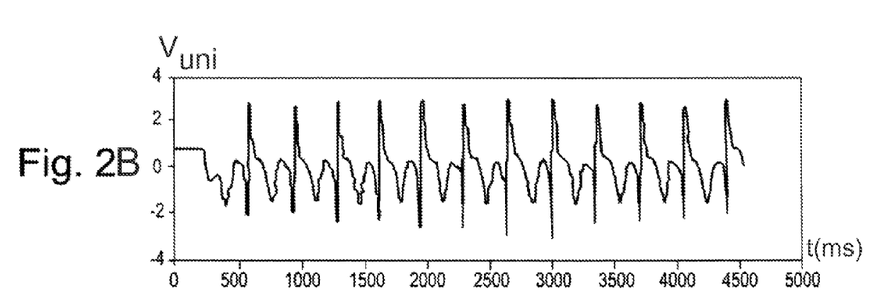

FIG. 2 shows exemplary plots of electrograms $V_{bip}$ and $V_{uni}$ obtained respectively from the bipolar ventricular channel (FIG. 2a) and the unipolar ventricular channel (FIG. 2b) according to the configuration shown in FIG. 1.

Figure 3:
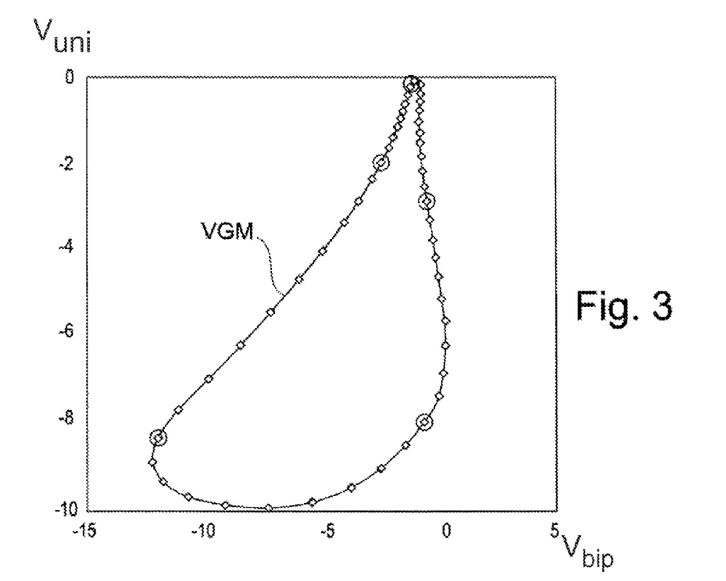
FIG. 3 shows a vectogram obtained from the two EGM signals of FIG. 2.

After these EGM signals are collected in the time domain, one of the EGM signals is traced with respect to the other. FIG. 3 shows an exemplary relative tracing characteristic of the EGM signals, referred to as a "cardiac loop" or "vectogram" (VGM). It should be understood that the vectogram VGM is distinguished from the "vectocardiogram" VCG that is obtained from external electrocardiogram ECG signals, and not from endocardial EGM signals.

The VGM is therefore representative of a heartbeat in a non-temporal space. It may be unnecessary to analyze the entire beat because the analysis of a significant fraction of the beat (typically the one centered on or about the corresponding QRS complex) is generally sufficient to detect an evoked wave.

More specifically, the beat that follows each stimulation pulse is isolated by a fixed window, for example, a window of a 100 ms width (corresponding to 100 points for a sampling frequency of 1000 Hz) shifted by 10 ms from the moment of the stimulation. The typical value of 100 ms allows for good isolation of the QRS complex to analyze its morphology, without including much surrounding noise, said noise corresponding to the baseline wave after the QRS period ends. The beats are simultaneously recorded on the ventricular bipolar channel ($V_{bip}$) and the ventricular unipolar channel ($V_{uni}$). The fraction of each of these beats contained within the window is displayed as a vectogram in a two-dimensional plane consisting of the bipolar channel in abscissa and the unipolar channel in ordinate. It should be understood that in this case the corresponding vectogram may not be a closed loop because it is only a part of the complete cardiac loop, i.e., the QRS complex isolated inside the window.

According to one embodiment, the present invention is directed to performing a capture test for detecting an evoked wave, by analyzing the vectogram. This analysis does not involve any temporal parameter. Instead, it involves measuring a level of capture (e.g., total capture, fusion, absence of capture) of the cavity or cavities stimulated by the device by:

ensuring that the therapy has been delivered on the different stimulated sites, particularly in the case of a CRT therapy in which it is essential that both ventricles are stimulated together;

assessing how the therapy has been delivered, for the purpose of patient monitoring especially if it is desirable to know if, by the application of optimized stimulation delays on hemodynamics characteristics of the patient, the optimization produces an effective capture or induces a fusion situation;

adapting the stimulation energy to be at the minimum level necessary, to reduce the energy consumption of the device and therefore increase its lifespan;

if necessary, adapting the pacing intervals.

Measuring a level of capture in accordance with the present invention may be done cycle by cycle, with an adjustment (or not) of the stimulation energy or the pacing intervals (e.g., atrioventricular delay (AVD) and/or interventricular delay (VVD)), depending on the stimulation response. These potential adjustments may be made at regular intervals, e.g., every six hours.

For a multisite device, in accordance with one embodiment of the present invention the presence of a capture is tested simultaneously on all stimulation sites. This is in contrast to known techniques that require ensuring a presence of a capture on each stimulated site, a capture measurement made separately at each programmed stimulation site.

According to one embodiment, the analysis of the vectogram for a capture test is an intrinsic analysis of the properties of the cardiac loop obtained from a stimulation cardiac cycle. Alternatively, the analysis is a comparative analysis that seeks a correlation between the characteristics of a vectogram of obtained from a stimulation cardiac cycle and the characteristics obtained from one or more reference cardiac cycles with known and determined conditions (e.g., capture, no capture, fusion).

Figure 4:
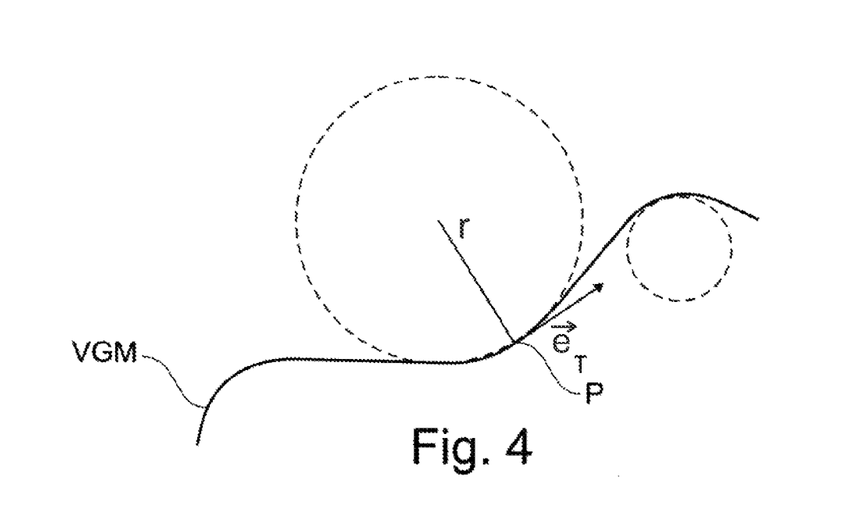
FIG. 4 illustrates exemplary parameters characterizing a vectogram at a given point, including the curvature and the tangent vector.

The following description is made in the context of a comparative analysis, but it should be understood that the present invention is not intended to be limited thereto, thus the present invention may be applied to an intrinsic analysis. In this embodiment, the vectogram is characterized by a descriptor based on a tangent vector $\vec{e}_T$ at a point P of the vectogram VGM, as shown in FIG. 4. It is possible to use other types of descriptors including the angle and a norm of the tangent vector $\vec{e}_T$.

The tangent vector $\vec{e}_T$ at a given point can be determined by a known technique, especially with a discrete filter that approximates the first derivative, for example, on four points at a sampling frequency of 1000 Hz.

Another descriptor that can be used is the curvature c (i.e., the inverse of the radius r) at a point P of the vectogram, for successively sampled points of the vectogram.

The tangent vector obtained for a stimulated cardiac cycle, i.e., a cardiac cycle to be analyzed, is compared to the corresponding vector of a reference curve that has been previously obtained for a reference cardiac cycle, for the same length, under reference conditions, preferably:

a complete capture on all stimulation sites in response to a stimulation pulse at high energy (i.e., an energy level that is high enough to ensure a capture), or by subsequent confirmation of the capture by a physician in light of the recorded reference cycles;

a partial capture of some of the stimulation sites: i.e., a stimulation pulse at high energy is delivered to selected sites where capture is wanted, with no stimulus or a stimulus at zero volts being delivered to the remaining sites; and a complete loss of a capture at all stimulation sites: i.e., by a stimulation at zero volts for all stimulation sites.

Any other situation that does not correspond to these three situations is considered a fusion situation.

Reference fusion curves may be created by adapting pacing intervals to spontaneous electrical events present in the considered cavity.

The reference vectograms are obtained either manually, by a test triggered by a practitioner who validates each reference type, or automatically, for the vectograms corresponding to a complete capture, a partial capture, and/or a complete loss of capture. In the latter case, the device regularly performs (e.g., every four hours, weekly . . . ) stimulation tests at high energy or at zero volts on different sites and updates the reference vectograms.

The method to make the comparison between a vectogram of a stimulation cardiac cycle and a reference vectogram will now be explained. This comparison uses a criterion derived from one or more descriptors to assess the degree of similarity or difference between the curves of each cardiac loop: e.g., the area circumscribed by the vectogram, the angle or norm of a tangent vector, the direction of travel, principal component analysis, or any other criterion for describing the morphology and orientation of the curve in the vector space. Depending on the degree of similarity observed, the device diagnoses a total capture, a partial or null capture, the degree of similarity being evaluated against a threshold that may or may not be linear. Preferably, the descriptor is the angle and/or the norm of the tangent vector $\vec{e}_T$ as shown in FIG. 4.

For a biventricular device, the acquisition and the prior memorization of a reference vectogram is performed by the following sequence of steps:

acquiring a reference cardiac cycle vectogram in a complete biventricular capture;

delivering biventricular pacing pulses over stimulation cardiac cycles (for example, eight cycles) at maximum energy;

acquiring a combined EGM for each of these stimulation cardiac cycles;

averaging the combined EGMs;

calculating a corresponding descriptive criteria; and storing the descriptive criteria of the complete biventricular capture.

The same technique is used for each type of reference vectogram: a right capture, a left capture, and a complete loss of a right and left capture. To ensure a capture, maximum energy is delivered to the selected site(s); to the contrary, to miss a capture, stimulation pulses are delivered with zero energy to the selected site(s).

Once a reference electrogram is acquired and stored, a capture test on a stimulation cardiac cycle is performed as follows:

stimulating the selected site(s);

acquiring a vectogram on the stimulated cardiac cycle event;

calculating a descriptive criteria of the vectogram so acquired;

comparing the descriptive criteria of the vectogram versus the reference vectogram in the complete biventricular capture.

If any discrepancies are found, a comparison is made with other reference vectograms (e.g., right capture alone, left capture alone), and if a difference still persists, it is determined to be a loss of a capture. At a loss of a capture, a security back-up stimulation of higher energy may be delivered.

The comparison of vectograms between a stimulated cardiac cycle with reference vectogram(s) is made by an algorithm such as those described in EP 2105843 A1 and its counterpart U.S. Pat. Pub. No. 2010/0249626 (assigned to Sorin CRM, previously known as ELA Medical), which describes various techniques for comparative analysis of electrograms in a specific application including a technique for discriminating between ventricular tachycardia and supraventricular tachycardia in a tachycardia classifier. EP 2105843 A1 and its counterpart U.S. Pat. Pub. No. 2010/ 0249626 are incorporated herein by reference. The vectogram comparison techniques described in EP 2105843 A1 and its counterpart U.S. Pat. Pub. No. 2010/0249626 are readily transferable to the implementation of the present invention, and they may be referred to for more details on the implementation of those vectogram comparison algorithms.

FIGS. 5-11 illustrate exemplary results of a capture test according to the present invention.

Figure 5:
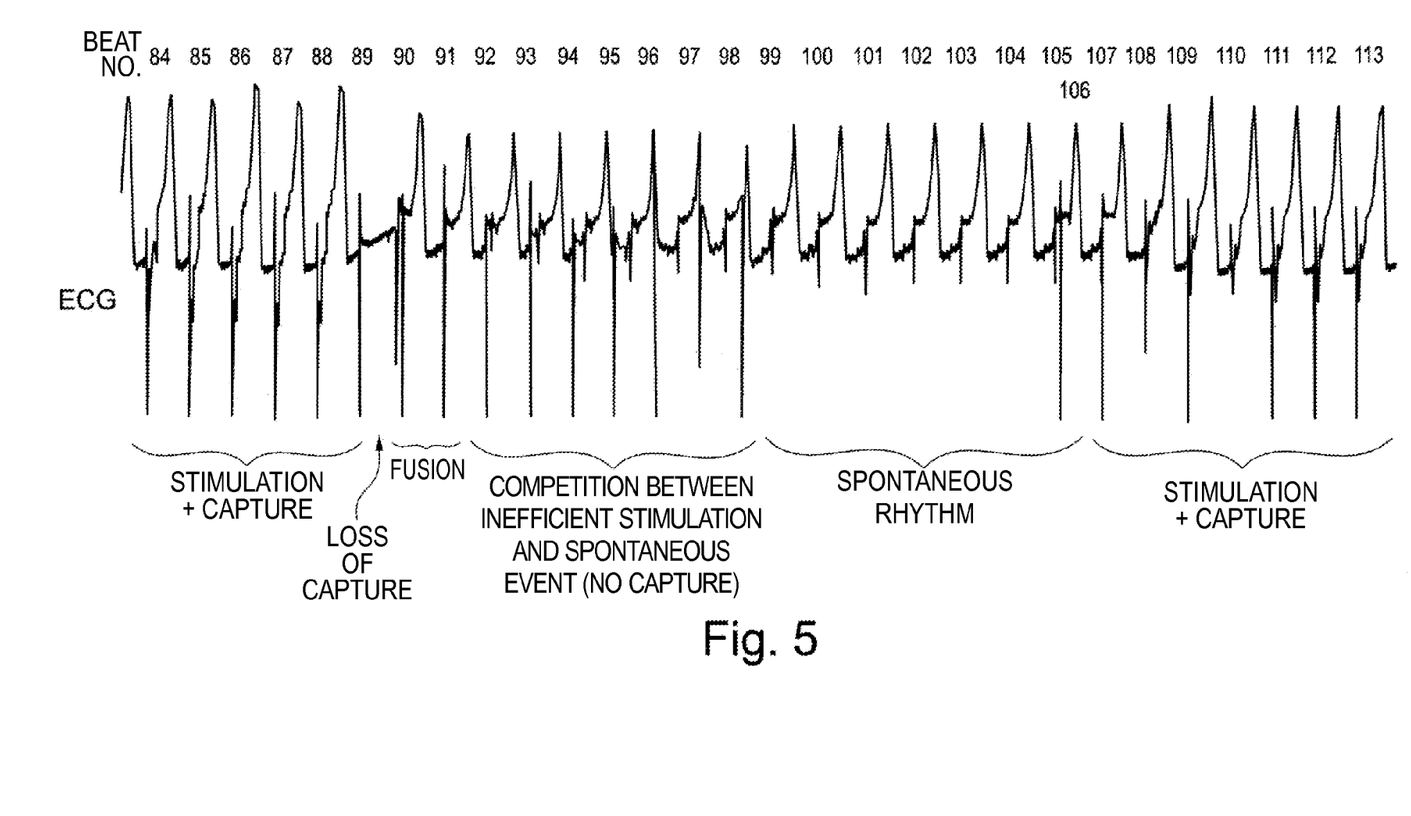
FIG. 5 shows an exemplary surface electrocardiogram illustrating, during successive beats, various situations that are taken into account by a detection algorithm.

FIG. 5 is a representation of a surface electrocardiogram (ECG) captured during an episode showing different situations such as a capture, a loss of a capture, a fusion, etc., each being representative of a typical situation encountered in real conditions.

FIGS. 6-11 show the electrocardiogram of FIG. 5. The left plot is the corresponding vectogram. The position of a descriptor X, evaluated by an characterization algorithm, is shown on the right plot in comparison with a decision boundary F between a capture and a loss of capture.

In this example, the retained criterion is a dual descriptor X combining first (horizontal axis), the value of the correlation coefficient between the norms of the respective tangent vectors of the analyzed vectogram and reference vectogram, and second (vertical axis), the average angle between the same tangent vectors respectively. Using these criteria, a field corresponding to the decision boundary F is defined such that if the dual descriptor X is within this area, it is considered to be a capture and if not, it is considered to be a loss of a capture. The area is represented by a rectangle corresponding to the criteria, for example, correlation coefficient >0.5 and average angle <70°.

Figure 6A:
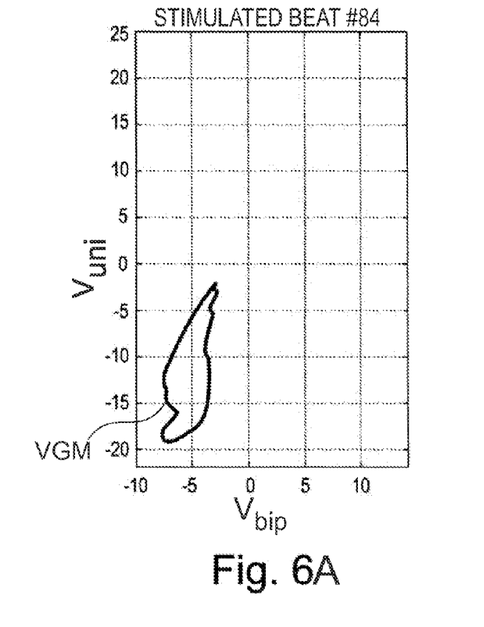
FIGS. 6-11 respectively illustrate, for various consecutive situations illustrated in the exemplary electrocardiogram of FIG. 5, the left plot corresponding to the vectogram and the right plot corresponding to the position of a descriptor evaluated by a characterization algorithm over a decision boundary between a capture and a loss of capture.
Figure 6B:
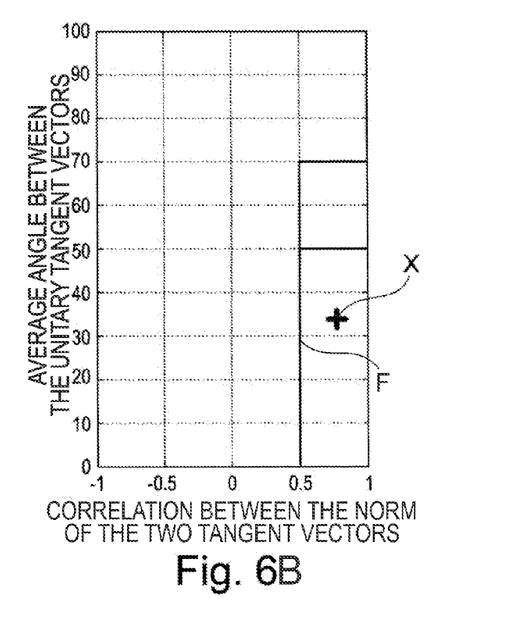
Figure 7A:
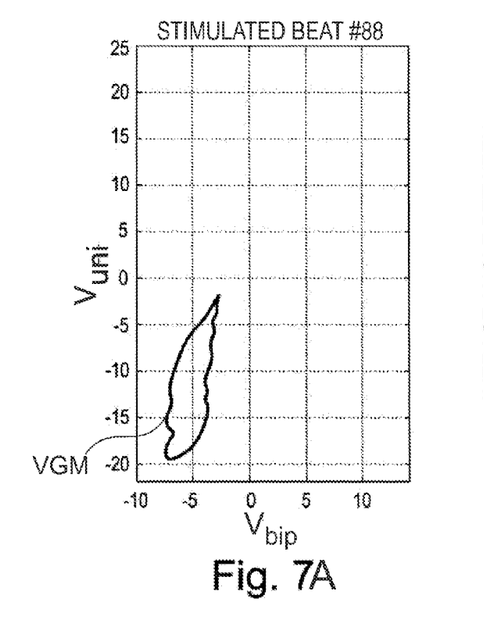
Figure 7B:
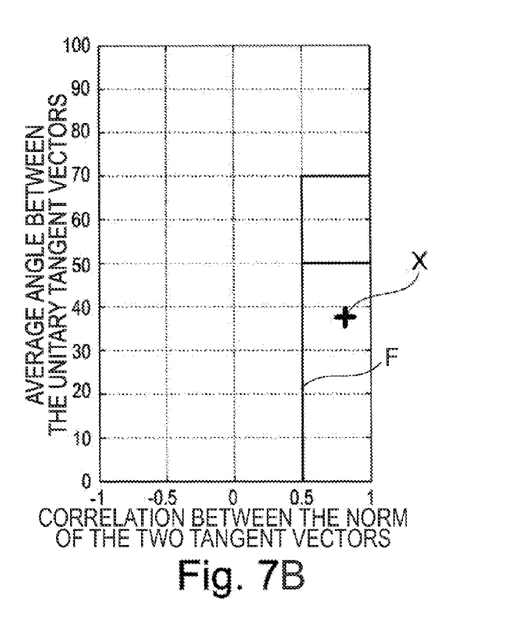

FIGS. 6 and 7 correspond to a situation of a complete capture of stimulated beats (beats No. 84 and 88 of the ECG in FIG. 5). It shows that the VGM has a regular shape, just before a loss of a capture (e.g., at beat No. 89). The dual descriptor X is situated within the decision boundary F.

Figure 8A:
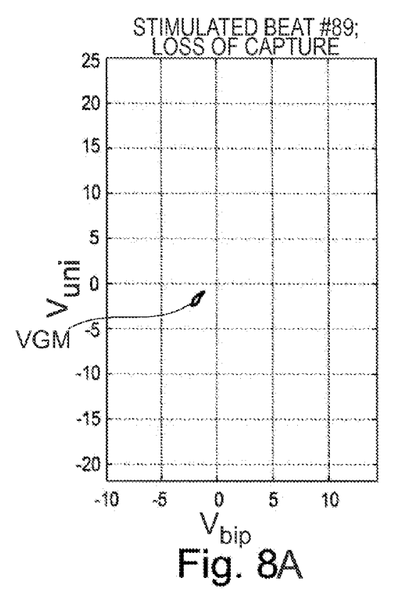
Figure 8B:
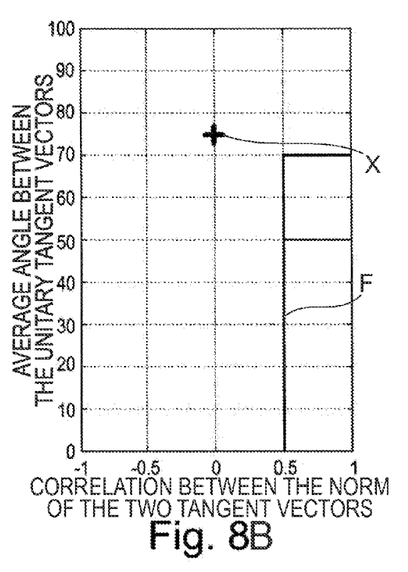

FIG. 8 illustrates a stimulated beat with a loss of a capture, corresponding to beat No. 89 of the ECG shown in FIG. 5. With the absence of a capture, the VGM is reduced to a very small loop. It is determined that a descriptor X is located substantially outside of the decision boundary F, including a correlation coefficient represented by the norms of tangent vectors being close to zero.

Figure 9A:
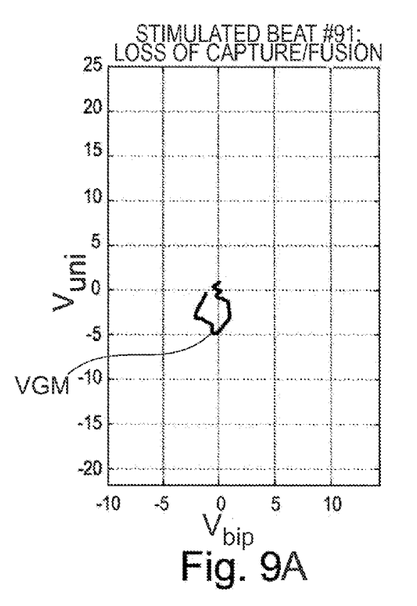
Figure 9B:
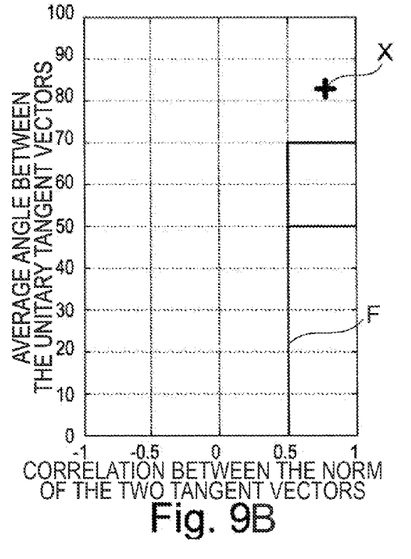

FIG. 9 shows a situation in which the absence of a capture is linked to the emergence of a fusion, corresponding to beat No's. 90 and 91 of the ECG shown in FIG. 5. In this situation (FIG. 9), it is shown that the shape of the vectogram is quite different from that of stimulation with a capture (FIGS. 6 and 7) and that of stimulation without a capture (FIG. 8). The analysis reveals, despite a relatively high correlation coefficient between the norms of tangent vectors, an average angle between the vectors significantly exceeds a prescribed threshold. The algorithm in this case determines that a loss of capture is only apparent, since it does not result from a natural increase in the pacing threshold, but is simply masked by the occurrence of a fusion.

The distinction between a proven loss of a capture and a fusion situation may be obtained, for example, by applying a criterion related to the area circumscribed by the vectogram. This area may be significantly larger in the case of a fusion (FIG. 9) than in the case of a true loss of a capture (FIG. 8).

Figure 10:
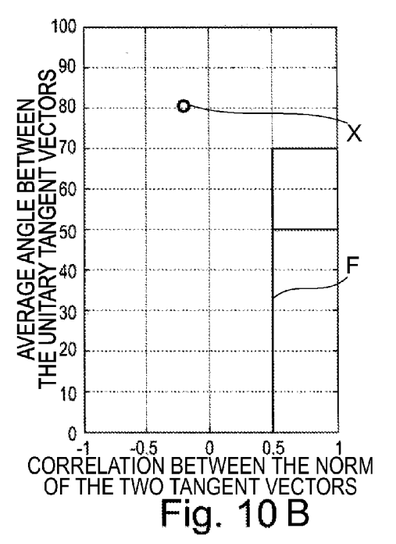
Figure 10A:
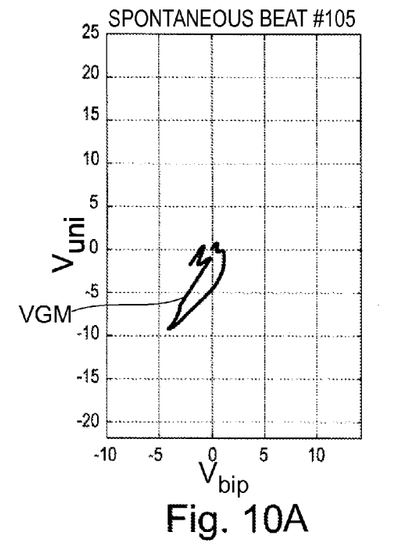

FIG. 10 illustrates a case of a beat in spontaneous rhythm, corresponding to beat No. 99 and following of the ECG shown in FIG. 5. In this case, the algorithm inhibits any capture threshold test because it is meaningless.

Figure 11A:
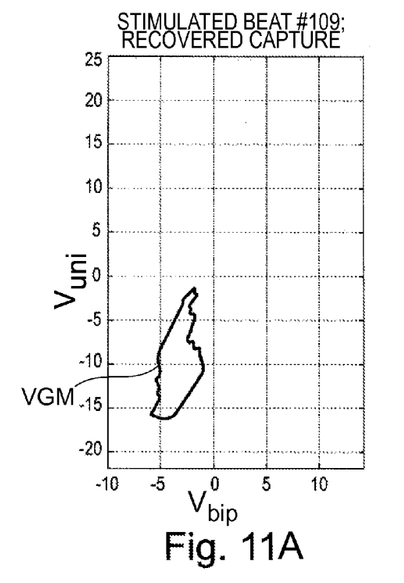
Figure 11B:
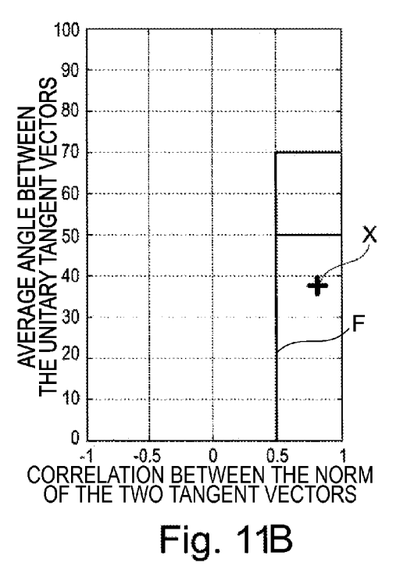

FIG. 11 illustrates a situation after disappearance of a spontaneous rhythm and resumption of stimulation and a capture, corresponding to beat No. 107 and following of the ECG shown in FIG. 5. The vectograms and descriptors X are somewhat similar to stimulation with a capture as shown in FIGS. 6 and 7.

According to one embodiment, a capture test according to the present invention is used to determine a pacing threshold. To this end, the device applies stimulation pacing pulses of decreasing energy to a cardiac cavity, and monitors a presence or absence of an evoked wave according to the monitoring technique described above. If a capture is confirmed at a given energy, the device considers that the stimulation is effective. The energy applied at the next cycle is reduced, typically by a fixed amplitude step, for example, 0.25 V. Once a capture is lost in this cycle, the device considers that the stimulation is ineffective, therefore determines that the pacing threshold is higher than the latest value applied. In this case, a back-up stimulation at the maximum amplitude may be applied to cause a contraction of the cardiac cavity.

The pacing threshold thus determined may be stored in a memory of the device, transmitted to a data collection center, or used by the device to change the stimulation amplitude for pacing.

For further details on algorithms for adjusting the stimulation amplitude from successive capture tests, one is referred in particular to EP 1080744 A1 and its counterpart U.S. Pat. No. 6,487,451 (Sorin CRM, previously known as ELA Medical), which describes various techniques for measuring the pacing threshold, for controlling consistency of measures and for adjustment of the width and amplitude of stimulation pulses, all of which are incorporated herein by reference. The corresponding algorithms may be implemented in a capture test performed by a vectogram analysis according to the teachings of the present invention.

Techniques other than those described above can also be implemented to analyze a vectogram and determine a presence or absence of a capture. In one particular embodiment, a principal component analysis ("PCA") may be applied to a vectogram. The PCA analysis is a technique in itself known that deduces the electrical axis of a heart and provides a general indicator of the direction taken by the electric wave when it propagates through the ventricle(s). The path with the highest dynamics is the one with the highest projection, the corresponding direction being called the "main axis." The main axis is supplemented by two other axes called "secondary axes", perpendicular to each other and to the main axis. In the present case, a two-dimensional analysis is performed, thus only one of the two secondary axes is considered. PCA is described in, for example, J. Shlens, "A Tutorial on Principal Component Analysis", 25 Mar. 2003, Version 1.

According to one embodiment, the PCA allows one to define the orthonormal basis to represent the vectogram $V_{uni}=f(V_{bip})$. If S1 and S2 designate signals on respective channels $V_{bip}$ and $V_{uni}$ representing a heartbeat, each signal consists of N points represented in the base of the electrodes $(V_{bip}, V_{uni})$ in which the coordinates of the ith point is $(S_1(i), S_2(i))$. For the principal component analysis, an assumption is made that these N points form an ellipse, and the axes of the ellipse that forms the PCA basis and the length of each axis are calculated. Using these two values, the main direction of the ellipse (i.e., the direction of spreading of the vectogram) is identified and, its size and area are quantified. The coordinates of these N points in the PCA base $(P_1, P_2)$ is sought by calculating a transition matrix from the base $(V_{bip}, V_{uni})$ to the PCA base $(P_1, P_2)$.

According to one embodiment, the principal component analysis extracts various parameters including the following descriptors:

the main axis that is the eigenvector of the covariance matrix associated with the largest eigenvalue;

the secondary axis that is the eigenvector of the covariance matrix associated with the second eigenvalue;

the size of the main axis and the secondary axis; and the angles between the two axes with respect to the axis OX, based on calculations of sines and cosines.

To extract the morphology of the vectograms from these PCA descriptors, each signal is projected on its own base. The corresponding one-dimensional signal is observed in the time domain and the forms are compared in order to detect a presence or absence of an evoked wave or to confirm indeterminacy because of a fusion situation.

One skilled in the art will appreciate that the present invention may be practiced by other than the embodiments described above, which are provided for purposes of illustration, and not of limitation.

The invention claimed is:

1. An active medical device comprising:
a pulse generator coupled to a lead for delivering electrical stimulation pulses of low energy to an electrode implanted in a heart chamber of a patient;
a microprocessor comprising circuitry for collecting electrical activity of the heart chamber, and configured for producing at least two distinct temporal components from two, concurrently collected, distinct electrogram intracardiac EGM signals of said heart chamber;
wherein the circuitry is further configured for performing a capture test on a stimulated cardiac cycle, the capture test comprising:
  detecting an occurrence of a depolarization wave induced by the stimulation pulses to the heart chamber during the stimulation cardiac cycle;
  determining a two-dimensional non-temporal characteristic (VGM) representative of said stimulated cardiac cycle based upon a relative tracing of one of said at least two distinct temporal components relative to the other of said at least two distinct temporal components; and
  performing a bi-dimensional analysis and delivering at least one descriptor parameter of said two-dimensional non-temporal characteristic, and determining a presence or a loss of a capture for said stimulated cardiac cycle based on said at least one descriptor parameter.

2. The device of claim 1, wherein the microprocessor is configured to collect a bipolar signal ($V_{bip}$) and a monopolar signal ($V_{uni}$), and wherein said at least two distinct temporal components comprises the bipolar signal ($V_{bip}$) and the monopolar signal ($V_{uni}$).

3. The device of claim 1, wherein the circuitry for performing the capture test is further configured to determine said at least one descriptor parameter from variations of said at least two distinct temporal components over time for a fraction of the stimulated cardiac cycle, said fraction including an QRS complex of said stimulated cardiac cycle.

4. The device of claim 1, wherein the circuitry for performing the capture test is further configured for comparing said two-dimensional non-temporal characteristic of the stimulated cardiac cycle to at least one two-dimensional reference characteristic obtained under a given set of conditions, the at least one descriptor parameter being representative of the degree of similarity or difference between the two-dimensional non-temporal characteristic and the at least one two-dimensional reference characteristics.

5. The device of claim 1, wherein the circuitry for performing the capture test is further configured for determining a fusion situation according to said at least one descriptor parameter.

6. The device of claim 1, wherein said at least one descriptor parameter is a geometric descriptor.

7. The device of claim 6, wherein the geometric descriptor is an angle of a tangent vector of the two-dimensional non-temporal characteristic at a plurality of points.

8. The device of claim 7, wherein the circuitry for performing the capture test is further configured for evaluating a correlation coefficient between angles of respective tangent vectors of the two-dimensional non-temporal characteristic of the stimulated cardiac cycle and of a two-dimensional reference characteristic.

9. The device of claim 6, wherein said geometric descriptor is a norm of a tangent vector of the two-dimensional non-temporal characteristic at a plurality of points.

10. The device of claim 9, wherein the circuitry for performing the capture test is further configured for evaluating a correlation coefficient between the norms of the respective tangent vectors of the two-dimensional non-temporal characteristic of the stimulated cardiac cycle and a two-dimensional reference characteristic.

11. The device of claim 10, wherein the circuitry for performing the capture test is further configured for evaluating a dual descriptor combining the value of the correlation coefficient of the between the norms of the respective tangent vectors of the two-dimensional non-temporal characteristic of the stimulated cardiac cycle and a two-dimensional reference characteristic and the average angle between the same tangent vectors.

12. The device of claim 11, wherein the circuitry for performing the capture test is further configured for determining a field corresponding to a decision boundary defined such that capture is confirmed if the dual descriptor is within the decision boundary and loss of capture is confirmed if the dual descriptor falls outside of the decision boundary.

13. The device of claim 12, wherein the decision boundary comprises an area wherein the correlation coefficient is less than 0.5 and the average angle between the tangent vectors is less than 70 degrees.

14. The device of claim 6, wherein said geometric descriptor is the curvature of the two-dimensional non-temporal characteristic at a plurality of points.

15. The device of claim 14, wherein the circuitry for performing the capture test is further configured for evaluating a correlation coefficient between respective curvatures of the two-dimensional non-temporal characteristic of the stimulated cardiac cycle and a two-dimensional reference characteristic.

16. The device of claim 6, wherein said geometric descriptor is an area circumscribed by the two-dimensional non-temporal characteristic.

17. The device of claim 1, wherein the circuitry for performing the capture test is further configured for performing a principal component analysis to deliver said at least one descriptor parameter.

18. The device of claim 1, wherein the device is a multisite device having a plurality of stimulation sites, wherein the pulse generator coupled to the lead delivers electrical stimulation pulses to selective ones of the plurality of stimulation sites, and wherein:
   the microprocessor is further configured for producing for each stimulation site of the plurality of stimulation sites said at least two distinct temporal components, and
   the circuitry configured for performing said capture test is further configured for discriminating among a presence of a capture on all of the plurality of stimulated sites; a presence of a capture only on a subset of the plurality of stimulated sites, and a loss of a capture at all of the plurality of stimulated sites.

* * * * *